US00PP26189P3

(12) United States Plant Patent
Egger

(10) Patent No.: US PP26,189 P3
(45) Date of Patent: Dec. 1, 2015

(54) ***SEDUM* PLANT NAMED 'ORBIT BRONZE'**

(50) Latin Name: *Sedum telephium (Hylotelephium telephium)*
Varietal Denomination: Orbit Bronze

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 121 days.

(21) Appl. No.: 13/987,671

(22) Filed: Aug. 20, 2013

(65) Prior Publication Data

US 2015/0059041 P1 Feb. 26, 2015

(51) Int. Cl.
*A01H 5/02* (2006.01)

(52) U.S. Cl.
USPC ..... Plt./479

(58) Field of Classification Search
USPC ..... Plt./479
See application file for complete search history.

(56) References Cited

PUBLICATIONS

Soos Grower Resources, Jul. 2013.*

* cited by examiner

*Primary Examiner* — Keith O. Robinson
(74) *Attorney, Agent, or Firm* — Klarquist Sparkman, LLP

(57) ABSTRACT

A new and distinct hybrid of *Sedum* plant substantially as shown and described, characterized by medium size, oblong, serrated leaves that are red brown in summer sun and olive green in spring, burgundy red stems, a high crown count that will grow or fill a container more quickly, an upright, round, tight habit like a topiary, and excellent vigor.

2 Drawing Sheets

Botanical denomination: *Sedum telephium* (*Hylotelephium telephium*).

Variety designation: 'Orbit Bronze'.

BACKGROUND OF THE INVENTION

The present invention relates to a new and distinct cultivar of *Sedum* and given the cultivar name of 'Orbit Bronze'. *Sedum* is in the family Crassulaceae. *Sedum* 'Orbit Bronze' is the result of a planned breeding project to produce short dark leaf *Sedum telephium* (*Hylotelephium telephium*) with high crown counts. The new cultivar originated from a cross between *Sedum telephium* 31-5, as the seed parent, and *Sedum telephium* 32-6, as the pollen parent. Both parents are proprietary, unpatented plants.

Compared to *Sedum telephium* 31-5, the new cultivar has a rounder, tighter habit.

Compared to *Sedum telephium* 32-6, the new cultivar has leaves that are more oblong, and less shiny, and the habit is rounder.

Compared to *Sedum* 'Chocolate Drop' (U.S. Plant Pat. No. 22,866), the new variety has a larger, rounder habit with a bigger crown faster, and with leaves that are oblong rather than oval.

This new and unique *Sedum* is distinguished by:

1. medium size, oblong, serrated leaves that are red brown in summer sun and olive green in spring,
2. burgundy red stems,
3. a high crown count that will grow or fill a container more quickly,
4. an upright, round, tight habit like a topiary, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the spring leaves of a 2 year old *Sedum* 'Orbit Bronze' growing outside in April in Canby, Oreg.

FIG. 2 shows a 9 month old in the trial field in September in Canby, Oreg.

FIG. 3 shows a 3 year old plant in September in the trial field in Canby, Oreg., showing the topiary habit.

FIG. 4 shows the flowers in late July to early August in Canby, Oreg.

DETAILED PLANT DESCRIPTION

The following is a detailed description of the new *Sedum* hybrid based on observations of two year old specimens grown in the garden in full sun under typical outdoor conditions in early August Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart,* 5th edition, 2007.

Plant:

*Type*.—Herbaceous perennial.

*Hardiness*.—USDA Zone 4 to 9.

*Size*.—49 cm tall from the ground to the top of the inflorescence and 45 cm wide.

*Habit*.—Erect, clumping.

*Vigor*.—Excellent.

*Roots and rooting*.—Main roots thick, with secondary roots dense and fibrous, color closest to Brown N200C in color; plants initiate roots in 10 days and produce a rooted plant in 4 weeks.

Stem:

*Number*.—About 21.

*Size*.—To 35 cm long and 10 mm wide.

*Internode length*.—4 mm to 5 mm long.

*Color*.—Greyed Purple 187A.

*Texture*.—Succulent.

*Surface*.—Glabrous, glossy.

Leaf:

*Type*.—Simple.

*Arrangement*.—Whorls.

*Shape*.—Oblong.

*Apex*.—Obtuse.

*Base*.—Cuneate.

*Venation*.—Pinnate.

*Margins*.—Serrate.

*Blade size*.—Grows to 6 cm long and 3.2 cm wide.

*Surface*.—Glabrous and matte on both sides.

*Petiole*.—Leaves sessile.

*Leaf color*.—Spring topside and bottom side closest to Yellow Green 147C including veins with margin Greyed Purple 187A; summer topside between Brown 200A and Greyed Purple N186B with main vein Greyed Purple 186C and leaf base where shaded Yellow Green 147A tinted Brown 200A; bottom side Yellow Green 147A tinted Greyed Purple 187A including vein.

Inflorescence:

*Type*.—Terminal, corymbose.

*Size of inflorescence*.—8 cm to 13 cm wide and 13 cm to 15 cm tall.

*Number of flowers*.—About 900 per stem (increases with stem size).

*Pedicels*.—1.5 mm to 2 mm long, 0.8 mm wide, glabrous, Greyed Purple N187B.

*Rachis*.—12 cm long and 6 mm wide at base, with about 10 side branches, Greyed Purple 187A.

*Bloom period*.—August through September in Canby, Oreg.

Flower bud:

*Size*.—2 mm wide, 4 mm deep.

*Description*.—Ovoid.

*Color*.—White 155C strongly marked with Greyed Purple N187D, darkest at tip.

Flower:

*Type*.—Complete, actinomorphic.

*Shape*.—Stellate.

*Size*.—3 mm deep and 5 mm wide.

*Corolla description*.—3 mm deep and 5 mm wide, 5 petals, each lanceolate, 3.5 mm long and 1 mm wide, margins entire, tip acuminate, glabrous on both sides, topside top half Greyed Purple 186B, bottom half Greyed Purple 186C, bottom side White 155C strongly marked with Greyed Purple N187D, darkest at tip.

*Calyx description*.—1.5 mm deep and 2 mm wide, stellate, 5 lobes, divided to the base, margins entire, tip acute, glabrous, Greyed Purple N187B on both sides.

*Stamen description*.—10 in number, 3 mm long, filaments 2.5 mm long, White N155A, anthers Yellow Orange 20B tinted Red Purple 60A, pollen Yellow 12B.

*Pistil description*.—3 mm wide and 2 mm deep, 5 separate prominent carpels, each 2.5 mm deep and 1 mm wide, style 0.5 mm long, Red Purple 61A overall.

*Fragrance*.—None.

*Lastingness*.—Each stem lasts up to a month.

Fruit:

*Type*.—Ventrally dehiscent follicle, erect, attenuate.

*Fertility*.—Poor.

*Color*.—Brown 200A.

Seed: Very small, Black 202A.

Disease and pest resistance or tolerance: Pest and disease resistance are typical for this type of *Sedum*. No problems noted in 5 years of growing in Canby, Oreg.

I claim:

1. A new and distinct hybrid of *Sedum* plant as herein illustrated and described.

* * * * *

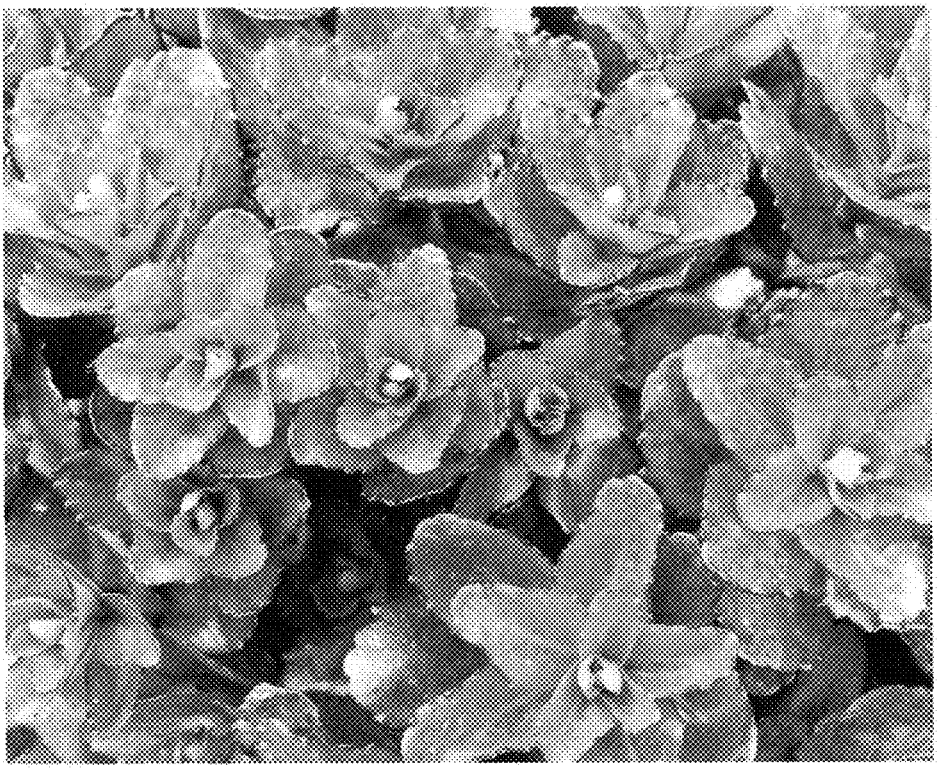
FIG. 1 above, FIG. 2 below
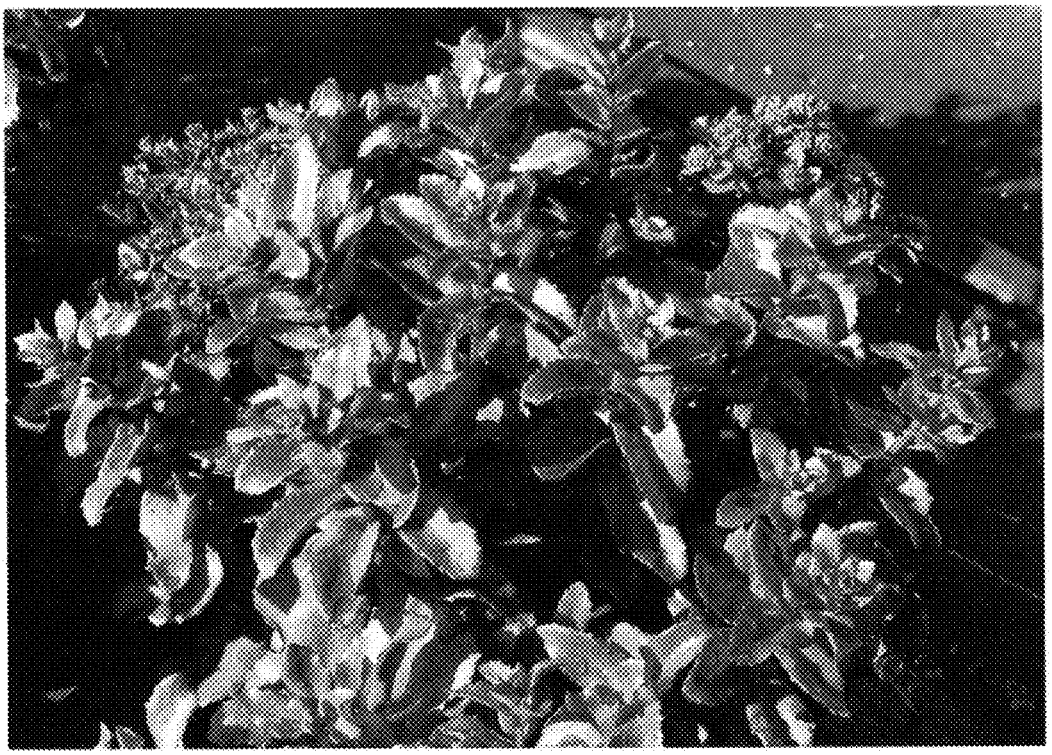

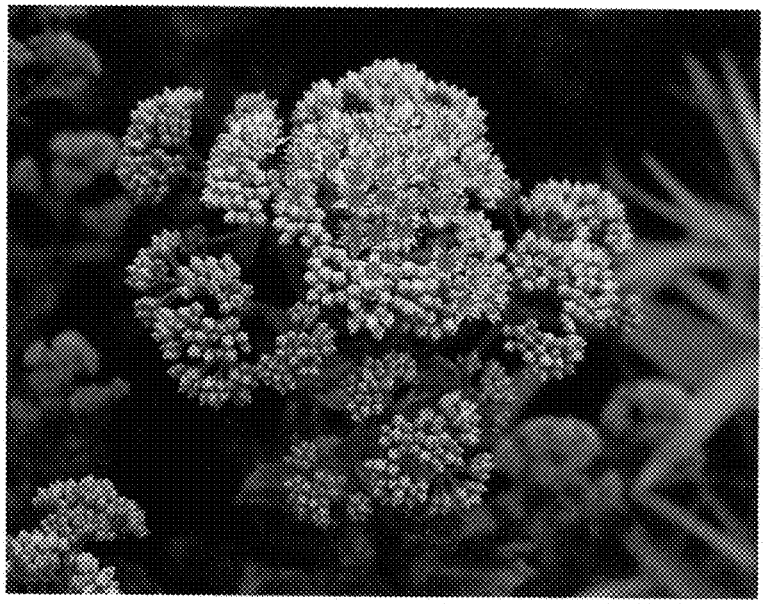

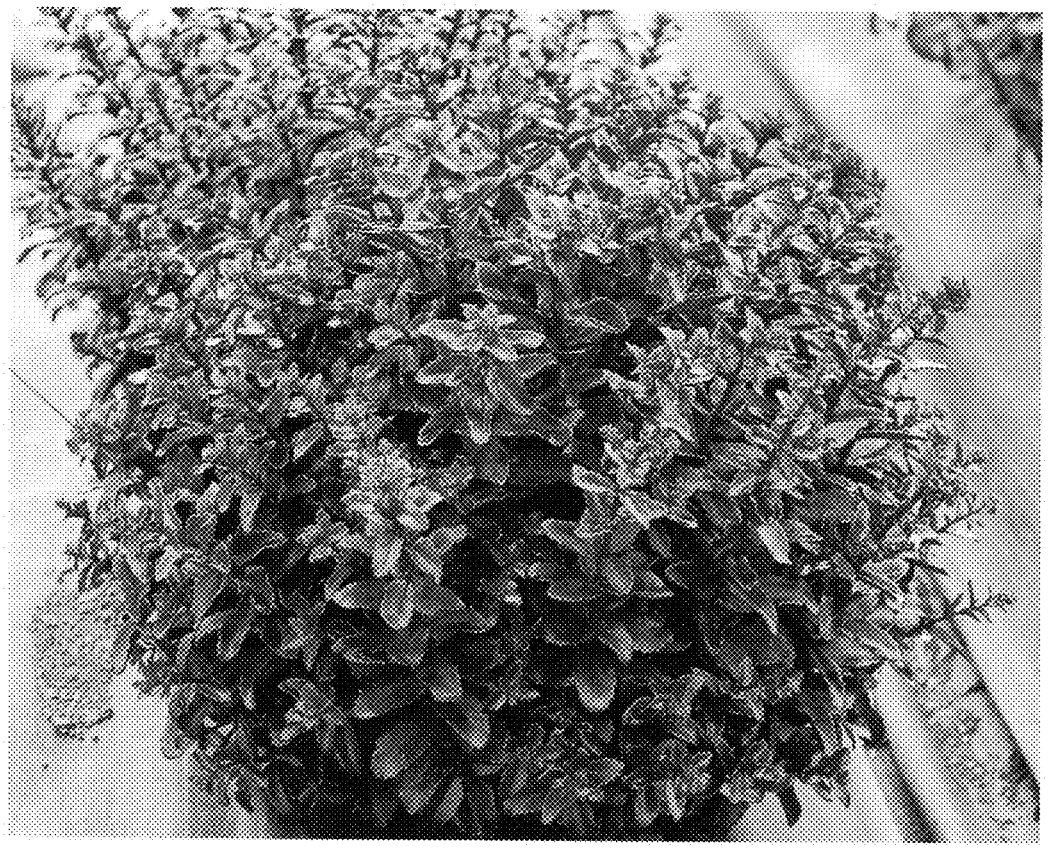
FIG. 3 above, FIG. 4 below